Figure 1:
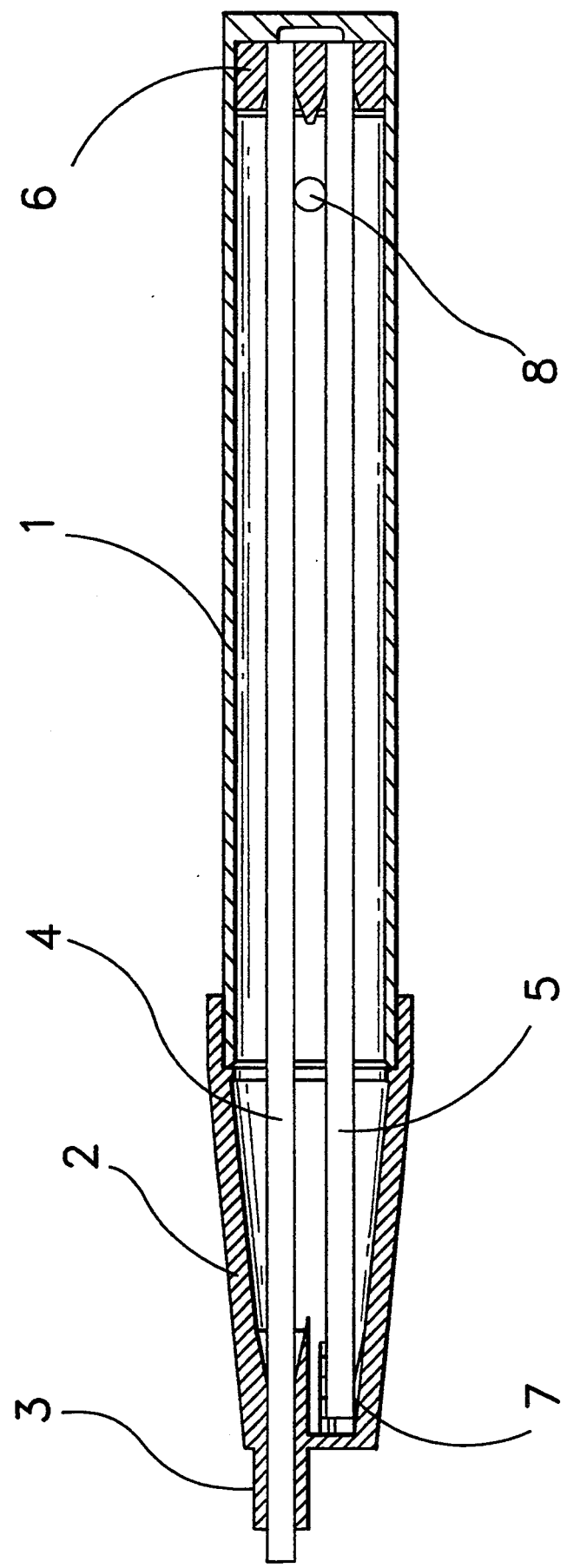

United States Patent [19]

Schwarz

[11] Patent Number: 5,386,834
[45] Date of Patent: Feb. 7, 1995

[54] APPARATUS FOR WITHDRAWING ARTERIAL BLOOD

[75] Inventor: Manfred Schwarz, Bachern, Germany

[73] Assignee: AVL Medical Instruments AG, Schaffhausen, Switzerland

[21] Appl. No.: 87,782

[22] PCT Filed: Nov. 14, 1991

[86] PCT No.: PCT/CH91/00234

§ 371 Date: Oct. 22, 1993

§ 102(e) Date: Oct. 22, 1993

[87] PCT Pub. No.: WO93/09714

PCT Pub. Date: May 27, 1993

[51] Int. Cl.$^6$ .............................. A61B 5/14
[52] U.S. Cl. ................... 128/765; 128/760
[58] Field of Search ............ 128/760, 761, 762, 763, 128/764, 765, 766

[56] References Cited

U.S. PATENT DOCUMENTS

| | | | |
|---|---|---|---|
| 3,630,191 | 12/1971 | Gilford | 128/762 |
| 3,645,252 | 2/1972 | Gilford | 128/762 |
| 4,020,831 | 5/1977 | Adler | 128/765 |
| 4,212,308 | 7/1980 | Percapio | 128/766 |
| 4,228,808 | 10/1980 | Marsoner | 128/762 |
| 4,964,832 | 4/1987 | Ungerstedt | 128/760 X |
| 4,980,297 | 12/1990 | Haynes et al. | 128/762 X |
| 5,000,193 | 3/1991 | Heelis et al. | 128/760 |

FOREIGN PATENT DOCUMENTS

| | | |
|---|---|---|
| 2836780 | 3/1979 | Germany . |
| 8902045 | 4/1989 | Germany . |
| 4015468 | 11/1991 | Germany . |

Primary Examiner—Sam Rimell
Attorney, Agent, or Firm—Ladas & Parry

[57] ABSTRACT

Apparatus for withdrawing arterial blood has a protective tube having a mounting member on one end of the tube. The mounting member includes a conical seat for the receipt of a hollow needle. A connecting member is mounted on the other end of the tube. First and second capillaries, having respective ends, are positioned within the tube. The first capillary is arranged concentrically within the second capillary so that an annular space is formed between the first and the second capillaries. The first capillary projects beyond both ends of the second capillary, and one end of each of the first and the second capillaries is mounted in the mounting member. The first capillary is connectable to a hollow-needle, and the other end of each of the first and the second capillaries is mounted in the connecting member which provides communication between the first and the second capillaries.

7 Claims, 4 Drawing Sheets

APPARATUS FOR WITHDRAWING ARTERIAL BLOOD

The invention relates to an apparatus for withdrawing arterial blood with a protective tube with mounting member, which includes a conical seat for the receipt of a hollow needle and two capillaries held in the protective tube of which the first is in communication with the hollow needle and the second via a deflecting member, in which the two capillaries are held in a seat, with the first capillary, whereby the ends of the capillaries facing away from the deflecting member are held in the mounting member and the protective tube and the mounting member for the hollow needle are made integrally.

A known apparatus for withdrawing blood of this kind is known from the DE 28 36 780 C2.

At a further known apparatus of this kind available under the trademark "MIKRO-PUNKTIONS-KIT" (Prospect of the company VAL Medical Instruments AG, Schaffhausen, Switzerland) the protective tube and the mounting member are made separately from each other, whereby the mounting member can be plugged onto the protective tube in a cap-like fashion. Apparatuses of this kind operate without the aid of the aspiration piston, whereby the blood flows into the hollow needle and from there into the capillaries due to the pressure of the blood. In order to transfer the withdrawn blood into a blood analysis apparatus the mounting member designed as cap is pulled off the protective tube, whereafter the capillaries can be pulled out of their seat in the deflecting member.

Due to a simple and safe mounting and also dismounting of the mounting member it has been produced at the known apparatus from a soft plastic material, preferably polyethylene. This material is, however, only translucent, therefore not clearly transparent. Accordingly, no safe checking of the last filling area of the second capillary is possible at this known apparatus. Also, due to the softness of the material no rigid connection between the hollow needle and the conical seat of the mounting member is possible. Therefore, there is the danger of an unintended detaching of the hollow needle from the mounting member, wherewith the operator may come into contact with the blood of the patient. The position-wise correct assembling in relation to the two capillaries of different length and also the demand of an easy to handle, small structural size led to the oval cross section of the known apparatus. This cross section is however quite difficult to control regarding leakage during the assembling of the deflection member onto the protective tube.

At the above mentioned known apparatus according to the DE 28 36 780 C2 the drawback of the loose mounting member which is designed as cap is overcome indeed because the mounting member and the protective tube are designed integrally, however, there still remains the drawback of the oval cross section of the protective tube because the two capillaries are still located adjacent each other.

Newer blood analysis apparatuses need due to a larger range of analyses a larger volume of blood. This is, however, without a decisive changing of the known apparatus attainable only via an enlarging of the inner diameter of the capillaries. This enlarging is, however, subject to limits. On the one hand the assembling and later removal of the capillaries out of the apparatus necessitate a certain stability, i.e. safety against breakage, and accordingly, a certain minimal wall thickness of the capillaries consisting of glass. On the other hand the diameter cannot be enlarged arbitrarily, because in order to obtain an impeccable blood analysis the blood must be prevented from a premature coagulation. For this reason the capillaries were heparinized at the surface of the inner side, i.e. provided with a chemical preventing a coagulation. The wettability, i.e. the action of the heparin onto the bloodstream in the capillaries decreases, however with a decreasing distance from the walls acted upon. Conclusively, it is possible that partial coagulations arise at the inside of the bloodstream which influence negatively the analysis.

The object of the invention is to provide an apparatus of the initially mentioned kind in such a manner that at an increased blood receiving volume a safe handling and a simplified assembling is possible.

In accordance with the invention there is provided an apparatus for withdrawing arterial blood comprising a protective tube (10) having a mounting member (11) on one end of said tube (10), said mounting member including a conical seat (15) for the receipt of a hollow needle, connecting member (23) mounted on the other end of said tube (10);

first and second capillaries (12, 13) having respective ends, and being positioned within said tube (10), the first capillary (12) being arranged concentrically within the second capillary (13) such that an annular space (14) is formed between said first and said second capillaries, said first capillary projecting beyond both ends of said second capillary, and one end of each of said first and said second capillaries being mounted in said mounting member (11), said first capillary (12) being connectable to a hollow needle, and the other end of each of said first and said second capillaries being mounted in said connecting member (23) thereby providing communication between said first and said second capillaries.

By the arrangement of the first capillary inside the second capillary a large volume is formed inside the second capillary in spite of the low thickness of the layer of the blood which accumulates between the first and the second capillary without that the total apparatus must be increased. Furthermore, the production of the protective tube and of the mounting member regarding the design of the respective seats for the capillaries is simplified by this arrangement stuck concentrically into each other.

A specifically advantageous embodiment of the invention is arrived at, in that the mounting member includes a pot-like collar surrounding the conical seat for the hollow needle and being opened in the direction of the tapered end of the conical seat, which is made integrally with the mounting member and includes a bayonet catch for the hollow needle. This bayonet catch allows a safe holding of the hollow needle on the conical seat.

An advantageous embodiment of the bayonet catch consists in that the collar comprises a substantially elliptically shaped insertion opening made to suit the two flange-like projections of the hollow needles generally available on the market, and two perforations located opposite of each other in the direction of the short axis of the ellipse, into which the two projections of the hollow needle engage in the arrested position. In connection with a further embodiment, according to which the limiting surfaces of the perforations facing the open side of the collar extend obliquely relative to the longitudinal axis of the protective tube, it is made possible depending on the kind of thread to obtain a tightening of the hollow needle on the seat such that an excellent seal can be arrived at between the hollow needle and this seat. Furthermore, an accidental detaching of the hollow needle from its seat is prevented by the form-locked engaging of the projections in the perforations, such that the handling of the apparatus is considerably safer than that of the known apparatuses, in which the hollow needles were apt to detach themselves from the seat due to a missing of a form-locked coupling.

The designing of a bayonet catch at a blood withdrawal apparatus for a mounting of the hollow needles is, however, basically known from the DE 30 49 503 A1. The hollow needle is held there at a cylinder shaped bushing which can be slid onto a cylinder shaped projection at the protective tube and includes a longitudinal slot having an end slot angled off at an obtuse angle, into which a peg-shaped arresting cam at the cylinder shaped projection of the protective tube engages. This coupling between hollow needle and protective tube is due to a missing of the tapering seat and the design of the bayonet catch in form of perforations in a collar surrounding the tapering seat and having oblique surfaces allowing a strong pressing of the hollow needle onto the conical seat not that safe and secure without having to resort to an additional seal. In contrast, at the known design an additional sealing of the hollow needles is necessary.

Because in accordance with a further embodiment of the invention the protective tube has a circular cross section, this makes not only a specifically compact design possible, but also a design of the respective seat surfaces for those ends which face the hollow needle is facilitated. This circular cross section is made possible by the concentrical arrangement of the capillaries.

It has been proven to be specifically advantageous if in accordance with a further embodiment of the invention the connecting member is designed as a plug of a soft plastic material and is releasably plugged into the protective tube and includes two concentric blind hole like bores for the receipt of the capillaries, of which the bottom of the bore serves as front side abutment for the capillaries and the inner bore includes at least one cross-slot which extends in radial direction up to the inner wall of the outer capillary and in longitudinal direction proceeding from the abutment for the outer capillary up into the abutment for the inner capillary. This design allows a simple retrieving of the capillaries out of the protective tube such that the danger of a breakage of the capillaries consisting of glass is reduced and accordingly a safe handling of the apparatus is ensured. Because the connecting member designed as plug is detachably plugged into the protective tube and because this plug consists of a soft plastic material, the substantial advantage is arrived at, that upon a forceful plugging of the hollow needle onto the seat at the mounting member no danger of breakage of the first capillary consists because on the one hand the plug is of a yielding nature and on the other hand can yield relative to the protective tube in case that first capillary projects due to production tolerances too far out of the mounting member such that the hollow needle can press against the capillary. At the known apparatus it was possible, that in such case a breakage of the first capillary could occur. By the arranging of at least one cross-slot two transferring possibilities from the inner capillary to the outer capillary are arrived at. Preferably two intersecting cross-slots are foreseen, such that four transfer possibilities exist.

If in accordance with a further advantageous embodiment the connecting member comprises a flange projecting radially over the protective tube and deviating from the circular shape, being preferably square, a rolling away of the apparatus having a circular cross section and placing onto a table is avoided.

Figure 2:
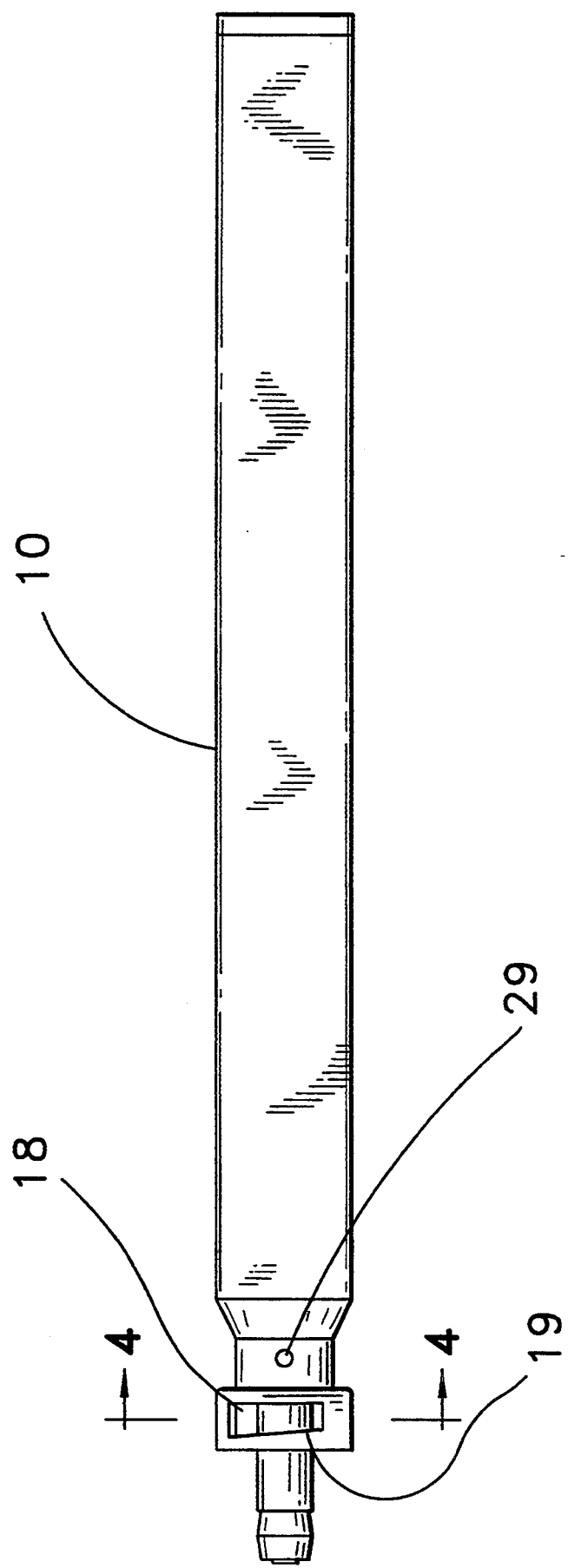
Figure 3:
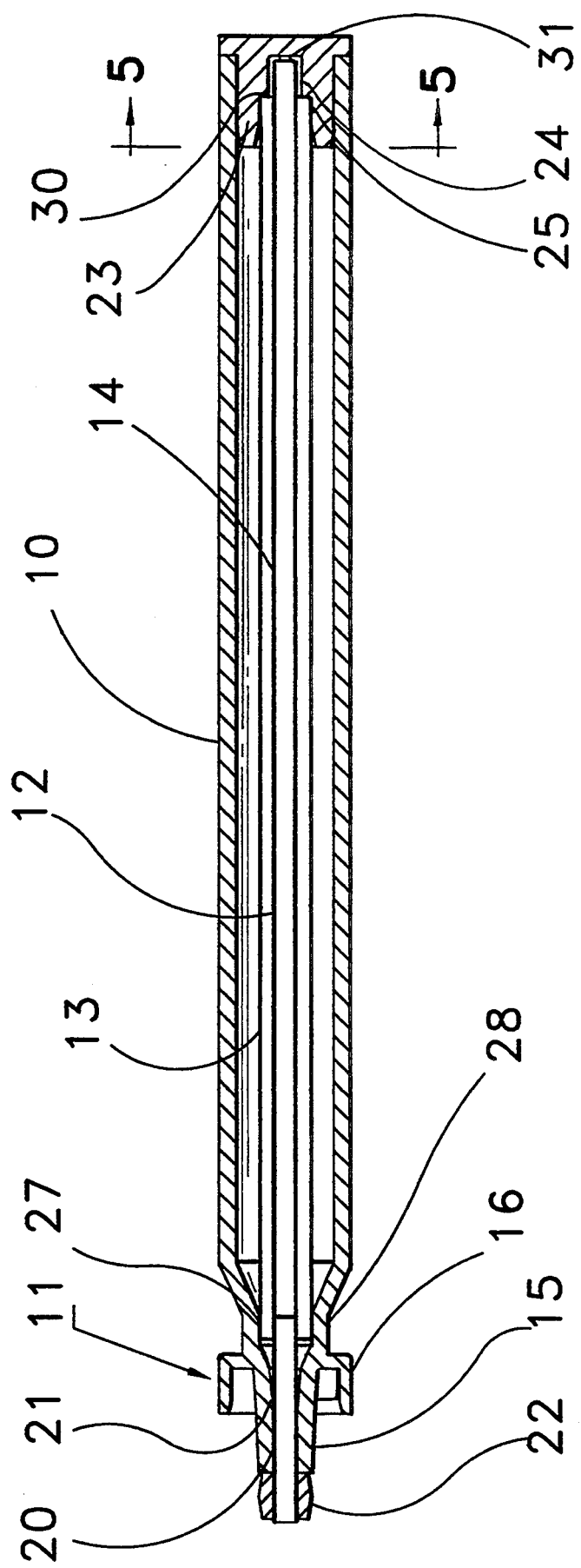
Figure 5:
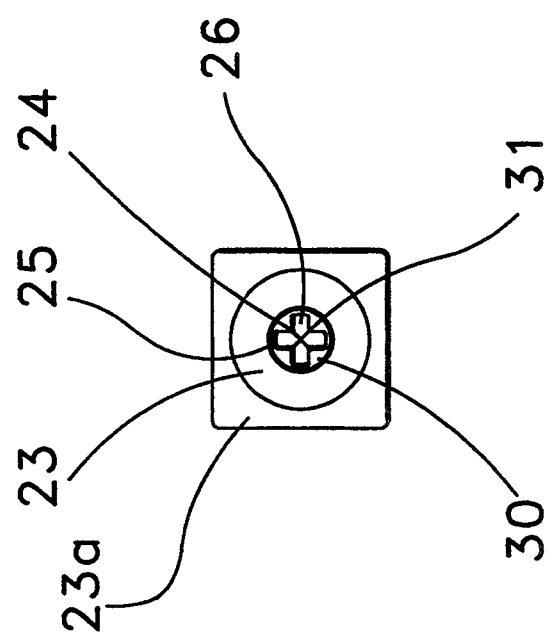
Figure 4:
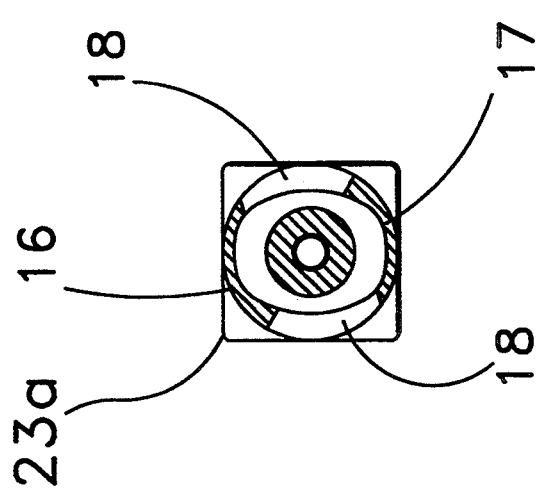

The invention will hereinbelow be explained more in detail based on a preferred embodiment. In the drawings there is shown in:

FIG. 1: a section through a known apparatus;

FIG. 2: a view of an apparatus in accordance with the invention;

FIG. 3: a longitudinal section through the apparatus according to FIG. 2;

FIG. 4: a section along line IV—IV in FIG. 2;

FIG. 5: a section along line V—V in FIG. 3.

The known apparatus according to FIG. 1 includes a protective tube 1, a mounting member 2 with a tapering seat 3 formed thereupon for a not illustrated hollow needle, a first capillary 4, a second capillary 5 and a connecting member 6. The first capillary 4 sits at its one end in the connecting member. At its other end the first capillary is held in the mounting member 2 and projects at this end somewhat over the tapering seat 3. The second capillary 5 sits also in the connecting member 6, which produces a communication between the first and the second capillary 4 and 5. The end of the second capillary 5 located opposite of the connecting member 6 is held in a seat 7 of the mounting member 2, which is plugged onto the protective tube 1. The protective tube 1 has a substantially oval cross section and consists of a transparent plastic material, whereas the mounting member 2 is made of a soft, only translucent plastic material which at its end, at which it is plugged onto, the protective tube 1 is made to suit the cross section of the protective tube. The mounting member tapers substantially conically in direction towards the conical seat 3. Two ventilation bores 8 are foreseen, which allow an exiting of air out of the protective tube during a filling of the capillaries. The capillaries are made of glass.

FIGS. 2 to 5 illustrate the inventive apparatus. It consists of a protective tube 10 of a circular cross section, at which a mounting member designated generally by 11 is integrally formed on. The protective tube 10 and the mounting member 11 consist of a transparent, relatively hard thermoplastic plastic material.

Two capillaries 12 and 13 extending concentrically to the protective tube 10 are arranged in this tube, whereby the first capillary 12 is set concentrically into the second capillary 13 such that an annular space 14 remains between the two capillaries.

The mounting member 11 comprises a tapering seat 15 on a nozzle-like projection 20 and a pot-like collar 16 surrounding same at the thicker end. The pot-like collar 16 limits, such as illustrated in FIG. 4, a substantially ellipse-shaped insertion opening 17 for a not illustrated hollow needle generally available on the market, which includes at its mounting end two opposite flange-like projections and is made to suit in this area the insertion opening 17. In the direction of the short axis of the ellipse-shaped opening 17 the collar 16 includes two perforations 18, of which the edges or limiting surfaces 19 facing away from the protective tube extend obliquely relative to the longitudinal axis of the protective tube such that the flange-shaped projections of the hollow needle set into the insertion opening 17 abut after a rotating of the hollow needle up to their engaging into the perforations 18 at this oblique surface 19, wherewith upon a further rotating of the hollow needle it is pulled positively onto the tapering seat 17 in a threadlike fashion. The collar 16 forms with its perforations 18 a bayonet catch which allows a form-locked arresting of the hollow needle at the mounting member 11.

The first capillary 12 is held on the one hand inside of the nozzle shaped projection 20 having a tapering seat 15 at its outer side, and which includes a through bore 21, which forms a seat for the first capillary 12. The capillary 12 projects outwards over the projection 20 and can be surrounded by a seal 22 in case specifically high demands are made regarding the sealing property.

The end of the second capillary 13 facing the mounting member 11 is held in a seat 27 of the mounting member 11, which is designed as through bore in a transition piece 28 having a decreased diameter relative to the protective tube 10.

The ends of the capillaries 12 and 13 opposite of the mounting member are plugged into a plug 23 designed as connecting member, which includes two concentrical blind hole-like bores 24 and 25, whereby the inner capillary 12, which projects over the outer capillary, is received in the bore 24 and the outer capillary in the bore 25. The respective bottom of the bore 30 and 31, respectively, of the bores 24 and 25 acts as front surface abutment for the capillaries 12 and 13. The inner bore 24 extending further into the plug 23 includes two cross-slots 26 located crosswise relative to each other, which extend in radial direction up to the inner wall of the outer capillary 13 and in longitudinal direction proceeding from the abutment 30 up into the abutment 31 such that they form four transitions or communications, resp., between the inner capillary 12 and the outer capillary 13. The blood flowing in the inner capillary 12 is guided via the slits 26 into the outer capillary. Because the protective tube 10 and the mounting member 11 consist of the same transparent material, it is possible to view during the withdrawal of the blood exactly how far the blood after the flowing out of the capillary 12 fills the annular space 14 via the slots 26 such that an exiting of blood at the end allocated to the seat 27 can be avoided.

The plug acting as connecting member 23 consists of a soft plastic material, such it can yield in case the first capillary 12 projects too far out of the mounting member and is pressed backwards by the hollow needle set thereupon. In order to take the capillaries out the connecting member 23 is pulled out of the protective tube 10, wherewith the two capillaries 12 and 13 can be pulled out with the protective tube 10. It is, hereto, necessary that the capillaries 12 and 13 are held in their corresponding seats stronger in the deflecting member 23 than at their opposite ends, which can be made possible due to the soft plastic material without any further difficulties. The capillaries taken out in this manner can be placed thereafter into a blood analyzing apparatus. Depending on the design of the blood analyzing apparatus it can, however, also be possible to place the capillaries together with the protective tube into the analysis apparatus. 29 identifies two opposite aerating bores in the protective tube.

The connecting member 23 includes a square flange 23a, which on the one hand facilitates a pulling out of the connecting member out of the protective tube because it acts as grip for this task and which on the other hand hinders a rolling away on a table.

What is claimed is:

1. Apparatus for withdrawing arterial blood comprising
   a protective tube (10) having a mounting member (11) on one end of said tube (10), said mounting member including a conical seat (15) for the receipt of a hollow needle,
   connecting member (23) mounted on the other end of said tube (10);
   first and second capillaries (12, 13) having respective ends, and being positioned within said tube (10). The first capillary (12) being arranged concentrically within the second capillary (13) such that an annular space (14) is formed between said first and said second capillaries, said first capillary projecting beyond both ends of said second capillary, and one end of each of said first and said second capillaries being mounted in said mounting member (11), said first capillary (12) being connectable to a hollow needle, and the other end of each of said first and said second capillaries being mounted in said connecting member (23) thereby providing communication between said first and said second capillaries.

2. Apparatus according to claim 1, wherein the conical seat (15) forms an integral unit with the mounting member (11), said conical seat tapering toward an end of said mounting member which is engageable with a hollow needle, and said mounting member further comprises a collar (16) surrounding the conical seat (15), said collar having an opening on one side for engaging a hollow needle, and said opening including a bayonet catch (18,19).

3. Apparatus according to claim 2, wherein the collar (16) has a substantially elliptically-shaped insertion opening (17), the opening having two perforations (18) located opposite of each other in the direction of the short axis of the ellipse, said perforations being engageable with two flange-like projections of a hollow needle.

4. Apparatus according to claim 3, wherein an edge surface (19) of each of the perforations (18) on the side of the collar (16) having an opening for engaging a needle, extends obliquely relative to the longitudinal axis of the protective tube (10).

5. Apparatus according to claim 1, wherein the protective tube (10) has a circular cross-section.

6. Apparatus according to claim 1, wherein the connecting member (23) comprises a plug of a soil plastic material which is releasably mounted to said protective tube (10), said connecting member having inner and outer concentric blind hole-like bores (24, 25) which serve as respective seats to receive the capillaries (12, 13), the base of each bore serving as an abutment (30, 31) for said capillaries, and the inner bore (24) having at least one cross-slot (26) which extends radially out to an inner wall of said second capillary (13) and in a longitudinal direction between the abutments (30, 31).

7. Apparatus according to claim 1, wherein the connecting member (23) further comprises a square flange (23a), which extends radially beyond the protective tube (10).

* * * * *

UNITED STATES PATENT AND TRADEMARK OFFICE
CERTIFICATE OF CORRECTION

PATENT NO. : 5,386,834
DATED : February 7, 1995
INVENTOR(S) : Manfred SCHWARZ

It is certified that error appears in the above-identified patent and that said Letters Patent is hereby corrected as shown below:

In column 6, line 53 (claim 6, line 2), "soil" should be -- soft --.

Signed and Sealed this

Thirteenth Day of June, 1995

*Attest:*

BRUCE LEHMAN

*Attesting Officer*     *Commissioner of Patents and Trademarks*

UNITED STATES PATENT AND TRADEMARK OFFICE
CERTIFICATE OF CORRECTION

PATENT NO. : 5,386,834
DATED : February 7, 1995
INVENTOR(S) : Manfred SCHWARZ

It is certified that error appears in the above-indentified patent and that said Letters Patent is hereby corrected as shown below:

Column 1, line 21, "VAL" should be -- AVL --.

Signed and Sealed this

Eighteenth Day of July, 1995

*Attest:*

BRUCE LEHMAN

*Attesting Officer*   *Commissioner of Patents and Trademarks*